(12) United States Patent
Cocco et al.

(10) Patent No.: US 9,361,003 B2
(45) Date of Patent: Jun. 7, 2016

(54) OVERLAY MAPS FOR NAVIGATION OF INTRAORAL IMAGES

(71) Applicant: Dental Imaging Technologies Corporation, Hatfield, PA (US)

(72) Inventors: George J. Cocco, Havertown, PA (US); Carsten Franke, Dusseldorf (DE); Michael J. Parma, Chalfont, PA (US); Louis P. Rubinfield, Glenmoore, PA (US); John Steck, Perkasie, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 531 days.

(21) Appl. No.: 13/797,248

(22) Filed: Mar. 12, 2013

(65) Prior Publication Data
US 2014/0115535 A1 Apr. 24, 2014

Related U.S. Application Data

(60) Provisional application No. 61/715,691, filed on Oct. 18, 2012.

(51) Int. Cl.
*G06F 3/0484* (2013.01)
*A61B 6/14* (2006.01)
*G06F 19/00* (2011.01)

(52) U.S. Cl.
CPC ............. *G06F 3/0484* (2013.01); *A61B 6/145* (2013.01); *G06F 19/321* (2013.01); *G06F 19/3406* (2013.01)

(58) Field of Classification Search
CPC ............. G06F 3/00; G06F 3/01; G06F 3/016; G06F 3/041; G06F 3/048; G06F 3/0481; G06F 3/0482; G06F 3/0484; G06F 3/0488; G06F 3/04883; G06F 3/04817; G06F 19/321; G06F 19/3406; G06T 7/004; G06T 7/0014; G06T 7/0024; G06T 2207/30036; G06T 2215/16; A61B 6/14; A61B 6/461; A61C 9/0053

See application file for complete search history.

(56) References Cited

U.S. PATENT DOCUMENTS

| | | | |
|---|---|---|---|
| 7,058,901 B1 | 6/2006 | Hafey et al. | |
| 7,339,573 B2 | 3/2008 | Andert et al. | |
| 7,731,495 B2 * | 6/2010 | Eisenberg et al. | 433/24 |
| 8,051,386 B2 * | 11/2011 | Rosander et al. | 715/810 |

(Continued)

FOREIGN PATENT DOCUMENTS

EP 1430830 6/2004

OTHER PUBLICATIONS

EP131647414 Extended European Search Report and Written Opinion dated Sep. 27, 2013 (6 pages).

(Continued)

*Primary Examiner* — Xiomar L Bautista
(74) *Attorney, Agent, or Firm* — Michael Best & Friedrich LLP (57) ABSTRACT

Methods and systems for viewing images. One system includes a source of images, a computer, and a screen. The computer includes a processor and a user interface module configured to generate a graphical user interface or GUI. The GUI includes a first window in which one or more of the images are displayed. The GUI is displayed on the screen and the graphical user interface module generates an output or modifies the GUI in response to user input (e.g., tap, click, etc.). In response to the input, the graphical user interface generates an image-navigation map. The image-navigation map is displayed in a foreground of the first window and the one or more images are in displayed in a background of the first window. The image-navigation map includes one or more thumbnail images of at least one of the one or more images.

20 Claims, 7 Drawing Sheets

(56) References Cited

U.S. PATENT DOCUMENTS

| | | | |
|---|---|---|---|
| 8,107,700 | B2 | 1/2012 | Daw et al. |
| 8,214,756 | B2 * | 7/2012 | Salazar-Ferrer et al. ..... 715/765 |
| 2005/0206658 | A1 | 9/2005 | Fagans |
| 2008/0063998 | A1 * | 3/2008 | Liang et al. ..................... 433/29 |
| 2008/0074511 | A1 | 3/2008 | Kramp et al. |
| 2009/0105578 | A1 | 4/2009 | Qu |
| 2009/0291408 | A1 * | 11/2009 | Stone-Collonge et al. ..... 433/24 |
| 2010/0315438 | A1 | 12/2010 | Horodezky et al. |
| 2011/0109650 | A1 | 5/2011 | Kreeger et al. |
| 2011/0311116 | A1 * | 12/2011 | Benn ............................. 382/128 |
| 2012/0096393 | A1 | 4/2012 | Shim et al. |
| 2012/0124506 | A1 | 5/2012 | Stuebe et al. |
| 2012/0172700 | A1 | 7/2012 | Krishnan et al. |
| 2013/0022251 | A1 * | 1/2013 | Chen et al. .................... 382/131 |
| 2013/0286174 | A1 * | 10/2013 | Urakabe ........................ 348/66 |

OTHER PUBLICATIONS

Sony, Reader Touch Edition User Guide PRS-650 (2010), 4-257-661-11(3), 139 pages.

Cockburn et al., Comparing Speed-Dependent Automatic Zooming with Traditional Scroll, Pan and Zoom Methods (2003), University of Canterbury. Computer Science and Software Engineering, 16 pages.

Liu et al., Automatic Browsing of Large Pictures on mobile Device (2003), MULTIMEDIA '03 Proceedings of the eleventh ACM international conference on Multimedia, 8 pages.

Rtiger et al., Zoom Navigation Exploring Large Information and Application Spaces (1996), AVI '96 Proceedings of the workshop on Advanced visual interfaces, 8 pages.

First Office Action from the Canadian Intellectual Property Office for Application No. 2,813,207 dated May 26, 2014 (2pages).

* cited by examiner

OVERLAY MAPS FOR NAVIGATION OF INTRAORAL IMAGES

RELATED APPLICATIONS

The present application claims priority to U.S. Provisional Application 61/715,691, filed Oct. 18, 2012, the entire contents of which are hereby incorporated by reference.

FIELD

Embodiments of the present invention relate to reviewing digital radiographic or photographic images.

BACKGROUND

Traditionally, navigating between images of a series, such as a series of intraoral images, requires opening numerous windows and continuously switching between image views. In particular, users are often required to exit a zoomed, full-screen viewing mode of one image to select another image within the same series or must view zoomed images sequentially.

SUMMARY

In some embodiments, the invention provides a graphical user interface with an overlay in the form of an image-navigation map. The image-navigation map, among other things, allows for faster and easier review of a series of images without leaving a zoomed, full-screen viewing mode. One particular embodiment takes the form of an image viewing system that includes a source of images and a computer having a processor and a user interface module. The user interface module is configured to generate a graphical user interface. A screen is connected to the computer and displays the graphical user interface. The graphical user interface has a first window in which at least one of the images is displayed. In response to user input (e.g., a cursor-control action such as a mouse click or tap of a touch screen), the graphical user interface generates an image-navigation map and the image-navigation map is displayed in a foreground of the first window. The at least one image is displayed in a background of the first window. The image-navigation map also includes one or more thumbnail images of the images.

In certain embodiments, the image viewing system is configured to operate in a first navigation mode and a second navigation mode. The first navigation mode is based on an image location within a series of images. The second navigation mode is based on anatomy. In a particular embodiment, the anatomy is dentition.

Another embodiment of the invention provides a method for controlling an image viewing system in a first navigation mode and a second navigation mode. The system includes a computer having a processor and a user interface module, and a screen connected to the computer. The method includes generating, by the user interface module, a graphical user interface, and displaying, on the screen, the graphical user interface including one or more images in a first window. The method also includes determining a location of a user input on the screen, and displaying, on the screen and in response to the user input, an image-navigation map in a foreground of the first window, and the one or more images in a background of the first window.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

Figure 1:
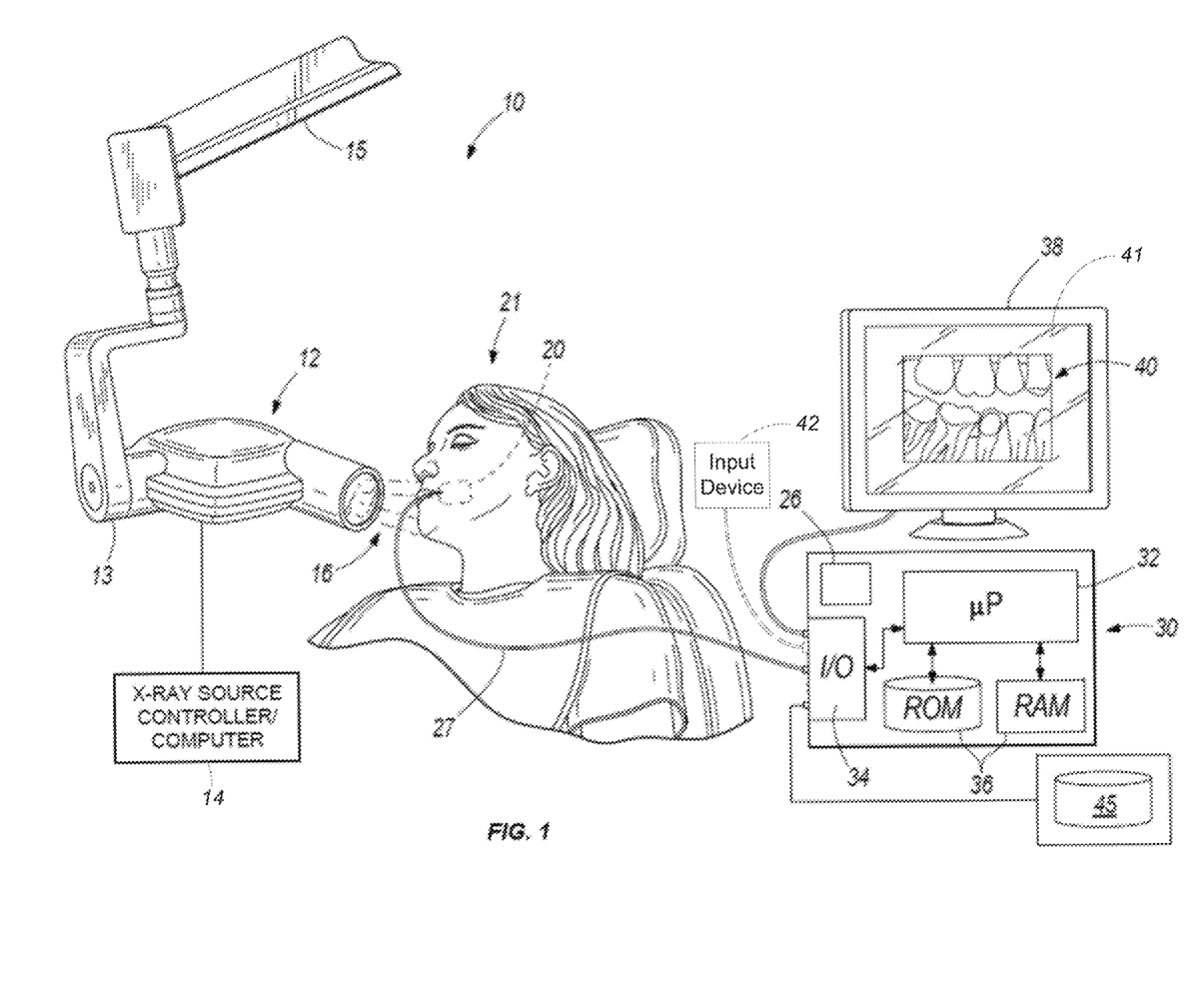
FIGS. 1 and 2 illustrate dental x-ray systems.

FIG. 1 illustrates a dental x-ray system 10. The system includes an x-ray source 12. In the embodiment shown, the source is located on an end 13 of a mechanical arm 15. When activated by an x-ray source controller 14, the x-ray source 12 generates an x-ray stream 16 that has a generally circular cross-section. (Of course, x-rays are generally invisible, but a representation of a stream is illustrated to facilitate understanding of the invention.) As shown in FIG. 1, x-ray source 12 is positioned (e.g., by an operator) so that the x-ray stream 16 is directed to an intraoral receptor 20. The intraoral receptor 20 is shown located in the mouth of a patient 21. In the illustrated embodiment, a wire, cable, or similar connector 27 of the receptor 20 connects the receptor 20 to a computer 30. However, the receptor 20 could communicate with the computer 30 wirelessly. Alternatively, as discussed in greater detail below, the receptor 20 could include memory for storing image data and, after an imaging procedure, could be removed from the patient's mouth and placed in a reader to retrieve the image data.

Although the system illustrated in FIG. 1 is an intraoral imaging system, the interface and other features of the present invention can also be used to display and navigate among images generated by panoramic and/or cone beam computed tomography (CBCT) systems, or even a set of images generated by different kinds of imaging systems, including for example intraoral, panoramic, and/or CBCT images, either individually or in combination.

The computer 30 includes various components, including a user interface module 26, a processor or similar electronic device 32, an input/output interface 34, and memory 36 (e.g., RAM and ROM). In some embodiments, the input/output interface 34 includes a universal serial bus ("USB") connection, and the connector 27 from the intraoral receptor 20 includes a USB cable. FIG. 1 illustrates that image data captured by the receptor 20 and processed by the computer 30 is sent to a screen 38 and viewed as an image 40. (Image 40 is drawn more distinctly than an x-ray image would typically appear.) In some embodiments, the image 40 is displayed on the screen 38 within a graphical user interface ("GUI") 41 generated by the user interface module 26.

In some embodiments, the screen 38 is a touch screen that is sensitive to a user's touch. Therefore, the touch screen allows a user to directly interact with the GUI 41 on the screen 38. In other embodiments, a user may use one or more input devices 42, such as a keyboard, mouse, joystick, etc., to interact with the GUI 41 on the screen 38. It should be understood that the terms "tap," "touch," "click," and "select" are used interchangeably within the present application to indicate a user selection (e.g., a cursor-control action) on the screen 38 made through a touch screen or with one or more input devices 42. In either embodiment, the screen 38 or device 42, as the case may be, is configured to generate an output or signal in response to a user touching a portion of the screen 38 or using a mouse or similar input device 42 to click on a portion of the screen 38. As illustrated in FIG. 1, images (i.e., data associated with a displayed image 40) may be stored in the memory 36, a database 45 coupled to the computer 30, or a combination thereof to provide a source of images.

In some embodiments, the screen 38 and the computer 30 are included in a tablet-type computer or smart phone.

Figure 2:
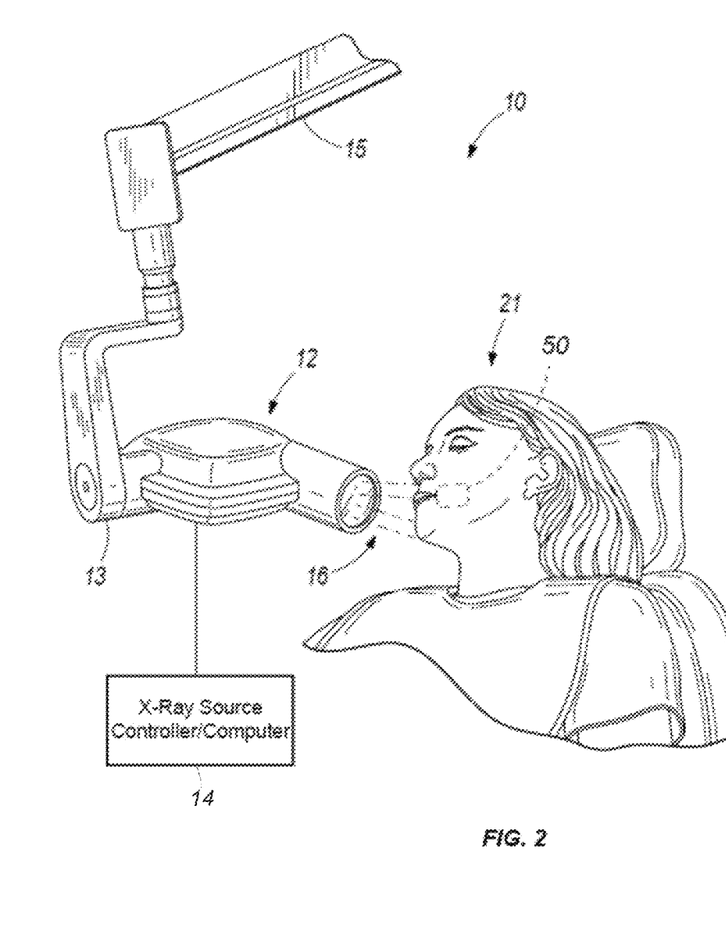

In some embodiments, as illustrated in FIG. 2, an image plate 50 is positioned in the mouth of the patient 21 in place of the intraoral receptor 20. The image plate 50 operates similar to the receptor 20, but stores collected data internally to memory included in the image plate 50 during a procedure. Therefore, no wire, cable, or similar connector is needed to connect the image plate 50 to the computer 30 during the procedure. Rather, to obtain the data stored to the image plate 50, a user inserts the image plate 50 into a reading device 60. The reading device 60 is configured to read information stored on the image plate 50 and transmit the information to the computer 30 (e.g., over a USB connection) for processing and display as described above with respect to FIG. 1.

The x-ray systems 10 illustrated in FIGS. 1 and 2 are examples of imaging systems that provide a source of images. Other imaging systems in which a series of images is generated could be used with the image-navigation overlay described below.

The user interface module 26 generates outputs (e.g., changes to the appearance of the GUI 41) in response to input or commands received from a touch screen or one or more input devices 42. The GUI 41 generated by the user interface module 26 is configured to allow a user to navigate images within a series of images. For example, an x-ray procedure typically generates a series of images of a portion of anatomy. Part of reviewing the series can include reviewing one or more of the images in the series independently and/or with reference to other images in the same series. As illustrated FIG. 3, the GUI 41 includes a window 82 in which one or more images 40 are displayed. While viewing an image 40 within the GUI 41, the user interface module 26 displays a next or previous image in the series when the user performs a first specified action (e.g., swiping on the touch screen or selecting or clicking a "NEXT" or "PREVIOUS" button) (not shown in FIG. 2). Alternatively, (as described in more detail with respect to FIG. 4 and other figures) the user interface module 26 displays an image-navigation overlay 84 when the user performs a second specified action (e.g., tapping or selecting the displayed image 40). The user interface module 26 displays at least some portions of the image-navigation overlay 84 in the foreground of the window 82 while continuing to display the image 40 in the background. Some of the portions of the image-navigation overlay 84 displayed in the foreground can be partially opaque and partially transparent to allow a user to view the displayed image 40 through portions of the image-navigation overlay 84.

Figure 4:
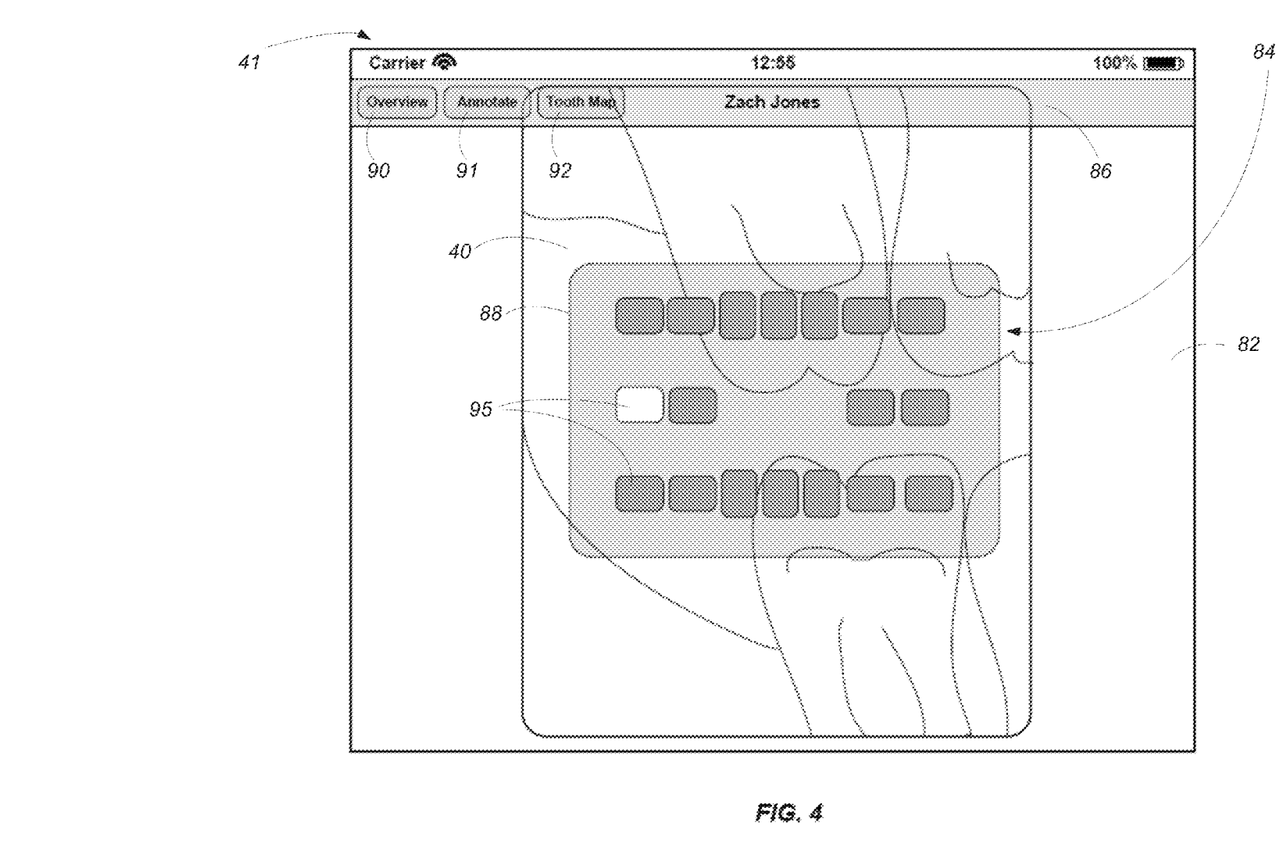

For example, FIG. 4 illustrates the GUI 41 displaying the image-navigation overlay 84 according to one embodiment of the invention. The image-navigation overlay 84 includes a menu 86 and an image-navigation map 88. The menu 86 includes at least three buttons: a first button 90, a second button 91, and a third button 92. The first button 90 is labeled "OVERVIEW," the second button 91 is labeled "ANNOTATE," and the third button 92 is labeled "TOOTH MAP." In some embodiments, the menu 86 also displays the name of the patient associated with a series of images (in this case "Zach Jones"). The user can select the "OVERVIEW" button 90 to return to previous screens displayed by the GUI 41 (e.g., an overview or starting screen for selecting a particular image series or a particular patient). A user can select the "ANNOTATE" button 91 to provide annotations for the displayed image 40. As described in more detail below, user can select the "TOOTH MAP" button 92 to view a tooth map within the image navigation overlay 84.

As illustrated in FIG. 4, the image-navigation map 88 includes thumbnail images 95 representing other images included in the selected series. In some embodiments, the thumbnail images 95 are arranged corresponding to the location of the patient's mouth that is displayed in each image 40. For example, images including the patient's right front teeth are represented by thumbnails 95 located on the top right of the image-navigation map 88. The user interface module 26 highlights one of the thumbnail images 95 based on the location of the currently-displayed image 40 within the series. As illustrated in FIG. 4, the image-navigation map 88 is displayed in a foreground of the window 82 and is at least partially transparent to allow a user to view the image 40 through the map 88. As described in more detail below, the image-navigation map 88 allows a user to quickly navigate between images of a series and provides location awareness within a zoomed-in or full-screen viewing mode.

Figure 5:
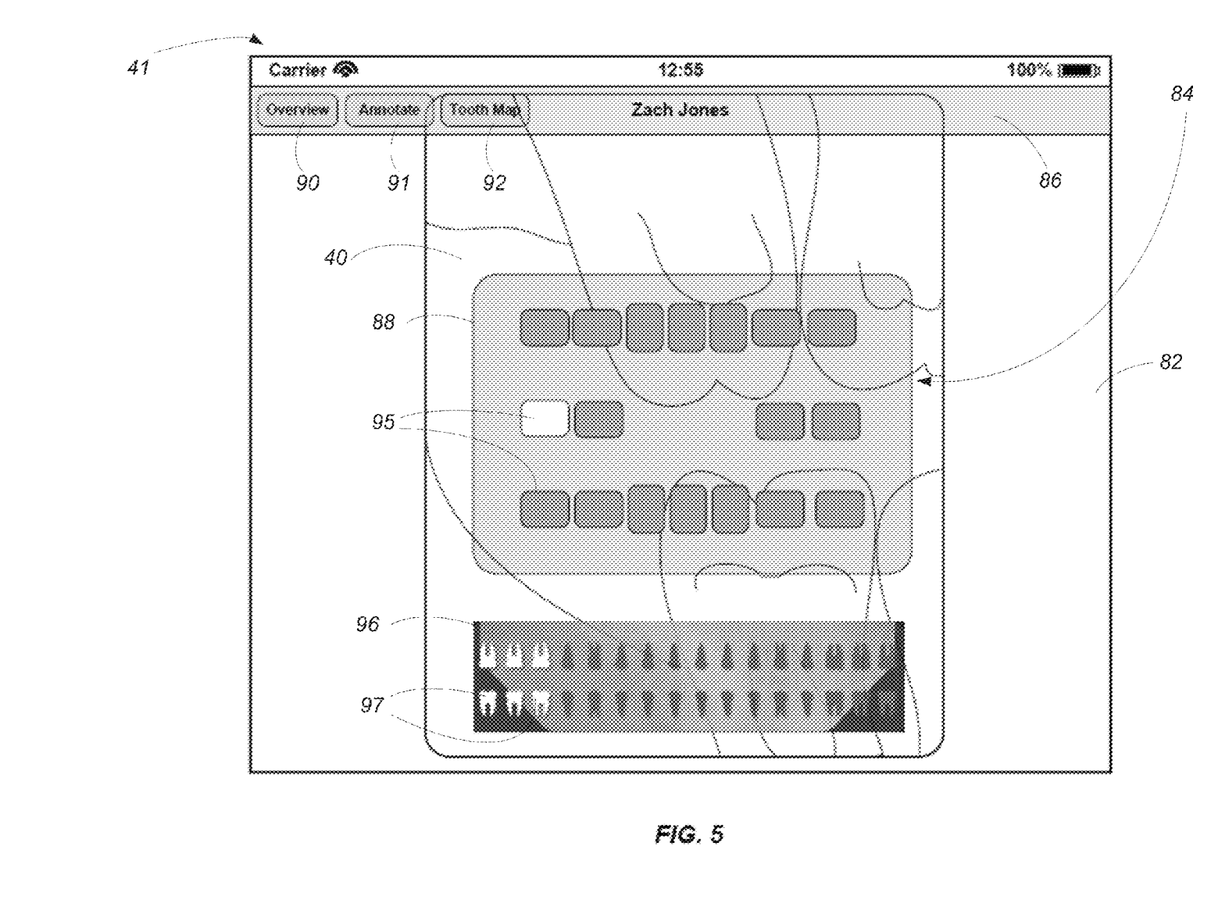

In some embodiments, the image-navigation overlay 84 includes a tooth map 96 in place of or in addition to the image-navigation map 88 (see, e.g., FIG. 5). The tooth map 96 includes small depictions 97 that graphically represent teeth. The user interface module 26 highlights one or more of the depictions 97 based on the anatomical region illustrated in the currently-displayed image 40. In some embodiments, the user interface 26 determines which depictions 97 to highlight based on metadata associated with a particular image, such as one or more tooth identifiers predefined for a particular image. As illustrated in FIG. 5, in some embodiments, the user interface module 26 simultaneously displays the tooth map 96 and the image-navigation map 88 within the image-navigation overlay 84. Similar to the image-navigation map 88, the tooth map 96 is displayed in a foreground of the window 82 and is partially opaque and partially transparent to allow a user to view the image 40 through the tooth map 86.

Figure 6:
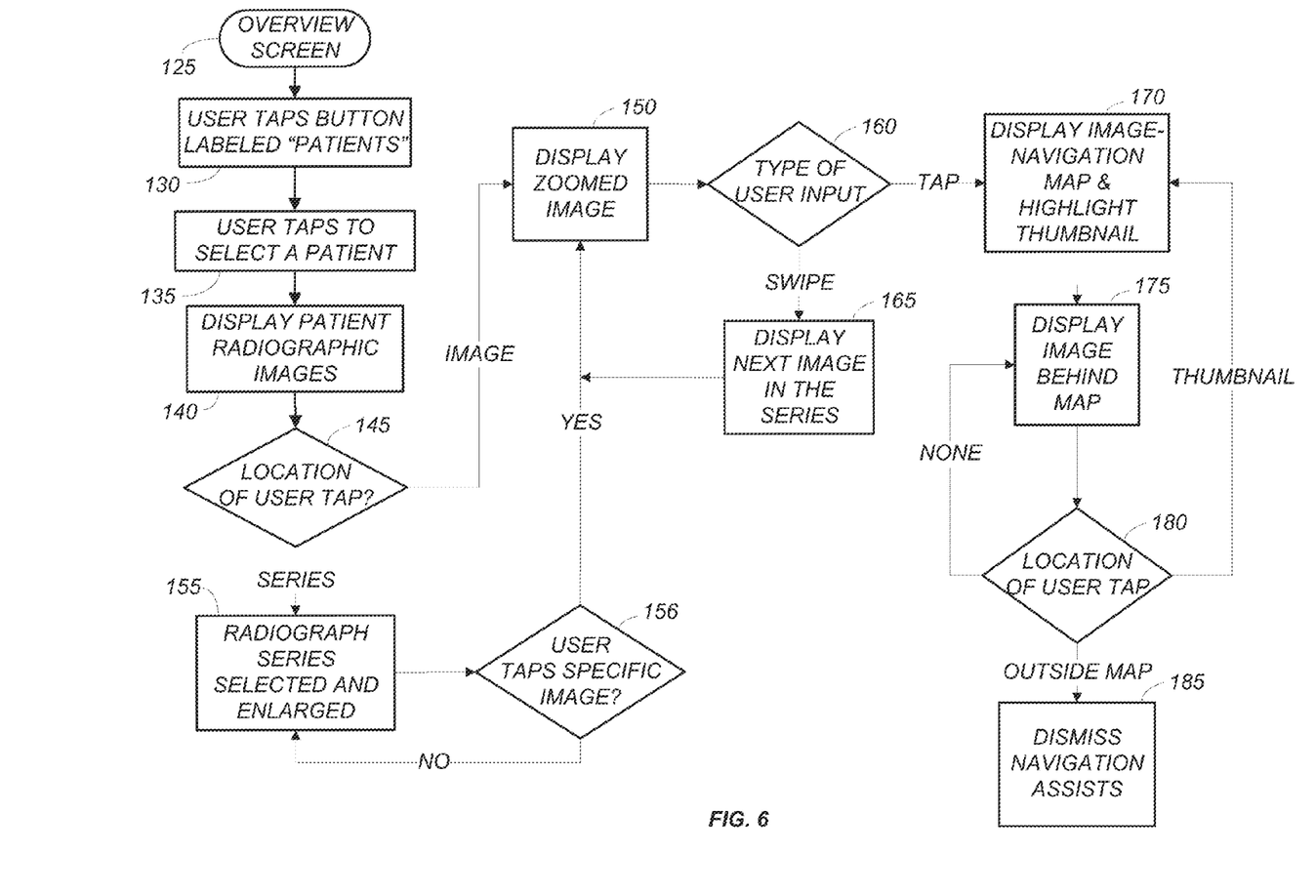
FIG. 6 is a flow chart illustrating a first mode of navigating images within the graphical user interface.
Figure 7:
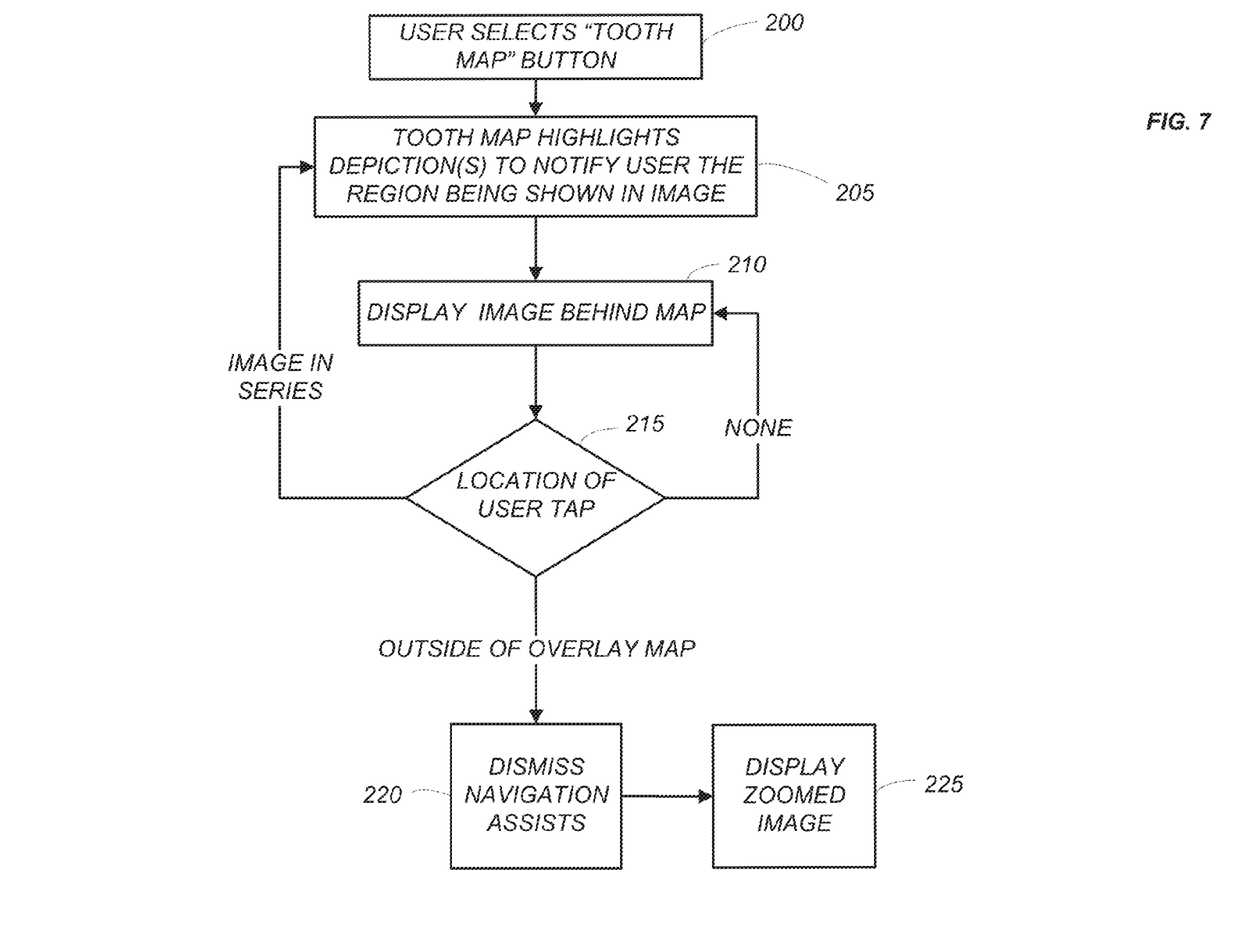
FIG. 7 is a flow chart illustrating a second mode of navigating images within the graphical user interface.

FIGS. 6 and 7 are flow charts illustrating navigation modes provided by the user interface module 26 when displaying images 40 in the GUI 41. In particular, FIG. 6 illustrates a first navigation mode for navigating between images based on an image location within a series of images. To select a particular series of images, the user interface module 26 initially displays an overview or starting screen within the GUI 41 (at 125). The starting screen displays options to a user for selecting an image for display. In particular, the starting screen includes a "PATIENTS" button. When the screen 38 includes a touch screen, the user can "tap" the "PATIENTS" button to select images associated with a particular patient. Alternatively, when the user uses an input device 42, for example, as a mouse or keyboard, the user can "click" on the "PATIENTS" button to select images associated with a particular patient. As noted above, it should be understood that the terms "tap," "click," and "select" are used interchangeably within the present application to indicate a cursor-control action or user selection, for example, touching the screen 38 or using an input device 42.

When the user selects the "PATIENTS" button (at 130), the user interface module 26 generates a list of available patients and displays the list in the GUI 41. When a user taps one of the patients in the list (at 135), the user interface module 26 displays one or more radiographic images 40 associated with the selected patient within the GUI 41 (at 140). As described above with respect to FIGS. 3-5, the GUI 41 has a first window 82 in which one or more images 40 are displayed.

After the images 40 are displayed, the user interface module 26 determines how the user wants to navigate the images 40 based on the location of a user tap (at 145). If the user directly taps on a particular image 40 within a series displayed in the GUI 41, the user interface module 26 displays the selected image 40 in the GUI 41 enlarged or zoomed (e.g., full-screen) (at 150). Alternatively, if the user taps on a series of images displayed in the GUI 41, the user interface module 26 displays the selected series enlarged (at 155). The user can tap on one of the images within the selected series (at 156), and, in response, the user interface module 26 displays the selected image 40 enlarged within the GUI 41 (at 150).

With a particular image 40 displayed enlarged in the GUI 41, the user interface module 26 waits for user input (at 160). If the user "swipes" the displayed image 40 (e.g., by dragging their finger horizontally across the screen 38), the user interface module 26 displays the next image in the same series (at 165). If the user taps the displayed image, the user interface module 26 displays the image-navigation overlay 84 (at 175). In the first mode of navigation, the overlay 84 includes the image-navigation map 88. As described above with respect to FIG. 4, the user interface module 26 displays the image-navigation map 88 in a foreground of the window 82 and continues to display the selected image 40 in the background of the window 82. The image-navigation map 88 is also at least partially transparent to allow a user to view the selected image 40 through the map 88. The user interface module 26 also highlights one of the thumbnails 95 included in the image-navigation map 88 that corresponds to the currently-selected image (i.e., the image 40 displayed in the background of the window 82). Therefore, the image-navigation map 88 highlights the location of a currently-selected image in a series of images. A user can select other thumbnails 95 displayed in the image-navigation map 88 to display a different image 40 within the GUI 41. Accordingly, a user can use the image-navigation map 88 to quickly identify and select a particular image of interest for display within the GUI 41.

In particular, returning to FIG. 6, with the image-navigation map 88 displayed, the user interface module 26 determines the location of subsequent user taps (at 180). If the user taps on a particular thumbnail 95 in the map 88, the user interface module 26 displays the image represented by the selected thumbnail 95 in the background of the window 82. In some embodiments, the user interface module 26 also displays the image-navigation map 88 in the foreground of the window 82 and highlights the thumbnail 95 included in the map 88 that corresponds to the newly-selected image (at 170). In other embodiments, the user interface module 26 only displays the newly-selected image and waits for the user to tap the image to display the image-navigation overlay 84 or portions thereof.

Figure 3:
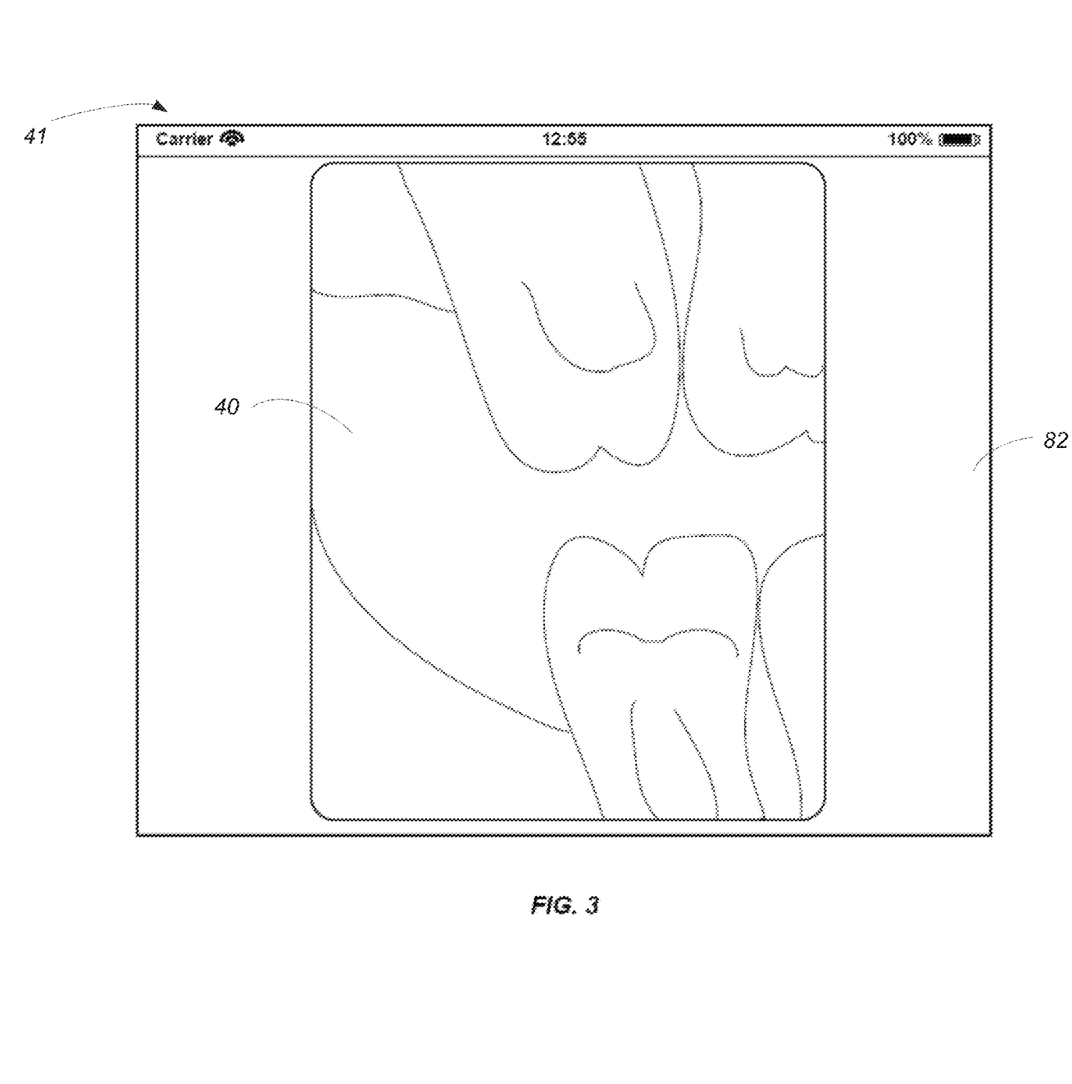
FIGS. 3-5 illustrate a graphical user interface displayed by systems such as those in FIGS. 1 and 2.

Alternatively, if the user taps on an area of the window 82 outside of the image-navigation map 88, the user interface module 26 dismisses the navigation assistance provided by the image-navigation map 88 and removes the image-navigation map 88 (and the entire image-navigation overlay 84) from view (see, e.g., FIG. 3). Therefore, the user interface module 26 effects navigation between a displayed image 40 and the image-navigation map 88 in response to where the user taps on the screen. Also, in some embodiments, a user can select a button from the menu 86 to re-display the image-navigation map 88.

FIG. 7 illustrates a second navigation mode for navigating between images based on anatomy, and, in particular, dentition anatomy. In this mode, the image-navigation overlay 84 displayed by the user interface module 26 includes a tooth map 96. In particular, if a user selects the "TOOTH MAP" button 92 from the menu 86 with a particular image 40 displayed within the GUI 41 (at 200), the user interface module 26 displays the tooth map 96 within the overlay 84 (at 205). As described above with respect to FIG. 5, the user interface module 26 displays the tooth map 96 in a foreground of the window 82 and continues to display the selected image 40 in the background of the window 82. The tooth map 96 is also at least partially transparent to allow a user to view the selected image 40 through the map 96. The user interface module 26 also highlights one or more of the depictions 97 based on the anatomical region illustrated in the currently-displayed image 40. Therefore, a user can quickly identify what teeth are displayed in a currently-displayed image 40. In some embodiments, as illustrated in FIG. 5, the user interface module 26 simultaneously displays the tooth map 96 and the image-navigation map 88 within the image-navigation overlay 84.

Returning to FIG. 7, with the tooth map 96 displayed, the user interface module 26 determines the location of subsequent user taps (at 215). If the user taps within the image-navigation map 88 (i.e., taps one of the thumbnails 95), the user interface module 26 displays the image corresponding to the selected thumbnail 95 in the GUI 41 behind the image-navigation map 88 (i.e., in the background of the window 82) (at 210), highlights the selected thumbnail 95 in the image-navigation map 88, and highlights one or more of the depictions 97 in the tooth map 96 based on the teeth included in the selected image (at 205). Therefore, as a user navigates through images using the image-navigation map 88, the tooth map 96 notifies the user of the particular teeth or region of teeth represented in the selected image.

If the user taps on an area of the window 82 outside of the image-navigation map 88, the user interface module 26 dismisses the navigation assistance provided by the overlap map 88 and the tooth map 96 and removes both maps from view (and the entire image-navigation overlay 84) (at 220). With the maps 88 and 96 no longer displayed, the GUI 41 only includes a selected image 40 (at 225) (see, e.g., FIG. 3). Accordingly, the user interface module 26 determines whether the user taps a region inside or outside of the image-navigation map 88 to determine whether to continue navigation assistance or dismiss navigation assistance. It should also be understood that in some embodiments, a user can directly select a particular depiction 97 within the tooth map 96 to select an image that includes the tooth associated with the selected depiction 97. In addition, in some embodiments, a user can dismiss the tooth map 96 (i.e., remove the tooth map 96 from view) by selecting the "TOOTH MAP" button 92 when the tooth map 96 is displayed.

Thus, embodiments of the invention provide, among other things, an image navigation overlay that includes one or more maps for navigating images within a particular series. The maps are displayed in a foreground of a window while a currently-selected image is displayed in the background. Because the maps can be at least partially opaque and at least partially transparent, a user can use the maps to navigate between images in a series while also viewing one of the images (e.g., in a zoomed, full-screen mode). It should be understood that the maps can be displayed based on particular user input (e.g., selecting or tapping a full-screen image) or can be displayed automatically as a user reviews images. Various features of the invention are set forth in the following claims.

What is claimed is:

1. An image viewing system comprising:
   a source of intraoral dental images;
   a computer having a processor and a user interface module, the user interface module configured to generate a graphical user interface, the graphical user interface having a first window in which at least one intraoral dental image from the source of intraoral dental images is displayed; and
   a screen connected to the computer and configured to display the graphical user interface;
   wherein, in response to at least one user input, the graphical user interface is configured to generate an image-navigation map and to display the image-navigation map in a foreground of the first window and the at least one intraoral dental image from the source of intraoral dental images in a background of the first window, wherein the image-navigation map is overlaid upon the at least one intraoral dental image, the image-navigation map including one or more thumbnail images of at least one of the intraoral dental images from the source of intraoral dental images, each of the thumbnail images indicating a predefined region of a patient's dentition, and wherein the thumbnail images are arranged to correspond to the patient's dentition.

2. The system of claim 1, wherein the image viewing system is configured to operate in a first navigation mode and a second navigation mode.

3. The system of claim 2, wherein the first navigation mode is based on an image location within a series of images.

4. The system of claim 1, wherein the image viewing system is configured to operate in at least one navigation mode is based on anatomy.

5. The system of claim 4, wherein the anatomy is dentition.

6. The system of claim 1, wherein the screen is a touch screen that configured to generate an output in response to at least one user input.

7. The system as claimed in claim 6, wherein the at least one user input is a tap of the touch screen.

8. The system of claim 1, wherein the user interface module effects navigation between an intraoral dental image and the image-navigation map in response to a user input on the screen.

9. The system of claim 1, wherein the image-navigation map is at least partially transparent.

10. The system of claim 1, wherein the user interface is configured to generate a tooth map, and wherein the tooth map is displayed simultaneously with the image-navigation map.

11. The system of claim 10, wherein the tooth map includes depictions that graphically represent teeth.

12. The system of claim 10, wherein the user interface module highlights one or more of the depictions in the tooth map based on the anatomical region illustrated in the currently-displayed at least one of the one or more intraoral dental images.

13. A method for controlling an image viewing system, the system including a computer having a processor and a user interface module, and a screen connected to the computer, the method comprising:
   generating, by the user interface module, a graphical user interface;
   displaying, on the screen, the graphical user interface including one or more intraoral dental images in a first window;
   determining a location of a user input on the screen; and
   displaying, on the screen and in response to the user input, an image-navigation map in a foreground of the first window and the one or more intraoral dental images in a background of the first window, wherein the image-navigation map is overlaid upon the one or more intraoral dental images, the image-navigation map including one or more thumbnail images of one or more intraoral dental images, each of the thumbnail images indicating a predefined region of a patient's dentition and wherein the thumbnail images are arranged to correspond to the patient's dentition.

14. The method of claim 13, further comprising controlling the image viewing system in a first navigation mode and a second navigation mode.

15. The method of claim 14, wherein controlling the image viewing system in the first navigation mode comprises highlighting an image location in a series of images.

16. The method of claim 13, further comprising controlling the image viewing system in at least one navigation mode, wherein controlling the image viewing system in the at least one navigation mode comprises highlighting an anatomical region of an image.

17. The method of claim 13, wherein determining the location of the user input on the screen comprises determining whether the location of the user input is in a region inside or outside the image-navigation map.

18. The method of claim 17, further comprising removing the image-navigation map from view when wherein the location of the user input is in a region outside of the overlay-image navigation map.

19. The method of claim 13, wherein the displaying, on the screen and in response to the user input, an image-navigation map includes displaying the image-navigation map so that it is at least partially transparent.

20. The method of claim 13, further comprising generating a tooth map, and displaying the tooth map simultaneously with the image-navigation map.

* * * * *